(12) United States Patent
Gould et al.

(10) Patent No.: US 6,656,719 B1
(45) Date of Patent: Dec. 2, 2003

(54) SERUM-FREE, LOW-PROTEIN MEDIA FOR ROTAVIRUS VACCINE PRODUCTION

(75) Inventors: Sandra L. Gould, Tinton Falls, NJ (US); David K. Robinson, New York, NY (US); Daniel J. Distefano, Cranford, NJ (US); T. Craig Seamans, Westfield, NJ (US)

(73) Assignee: Merck & Co., Inc., Rahway, NJ (US)

( * ) Notice: Subject to any disclaimer, the term of this patent is extended or adjusted under 35 U.S.C. 154(b) by 550 days.

(21) Appl. No.: 09/176,492

(22) Filed: Oct. 21, 1998

Related U.S. Application Data

(60) Provisional application No. 60/063,301, filed on Oct. 27, 1997.

(51) Int. Cl.⁷ ............................ C12N 7/00; C12N 9/76; C12N 9/99
(52) U.S. Cl. .................. 435/235.1; 424/213.1; 424/184.1
(58) Field of Search ...................... 435/235.1; 424/213.1

(56) References Cited

U.S. PATENT DOCUMENTS 4,205,131 A * 5/1980 Almeida ...................... 435/235

OTHER PUBLICATIONS

Bettger, W.J., Boyce, S.T., Wathall, B.J. and Ham, R.G. Rapid clonal growth and serial passage of human diploid fibroblasts in a lipid–enriched synthetic medium supplemented with epidermal growht factor, insulin, and dexamethasone. P.N.A.S. 78(9): 5588–55, Sep. 1981.*

Taub, M. and Livingston, D. The Development of Serum–Free Hormone–supplemented Media for Primary Kidney Cultures and thier use in Examining Renal Functions. Annals of the N. Y. Academy of Science. pp 406–421, 1981.*

Graham, et al., "Proteolytic Enhancement of Rotavirus Invectivity: Biologic Mechanism", Virology, vol. 101, 1980, pp. 432–739.

Bettger, et al., "Rapid clonal growth and serial passage of human diploid fibroblasts in a lipid–enriched . . . ", Proc. Natl. Acad. Sci., USA, vol. 78, No. 9, 1981, pp. 5588–5592.

Bake, et al., "Dexamethasone modulates binding and action of epidermal growth factor in serum–free . . . ", Proc. Natl. Acad. Sci. USA, vol. 75, No. 4, Apr. 1978, pp. 1882–1886.

Zhaolie, et al., "A Novel Serum–Free Medium For The Cultivation of Vero Cells on Microcarriers", Biotechnology Techniques, vol. 10, No. 6, Jun. 1996, pp. 449–452.

Clark et al., "Serum Supplements and Serum–Free Media: Applicability for Microcarrier Culture . . . ", Develop. Biol. Standard, vol. 50, 1983, pp. 81–91.

Merten, et al., "Evaluation of the new serum–free medium (MDSS2) for the production of different . . . ", Cytotechnology, vol. 14, 1994, pp. 47–59.

Van Donsel, et al., "Comparative Thermal Resistance of Human and Simian Rotaviruses Assayed . . . ", J. of Food Protection, vol. 49, No. 10, Oct. 1986, pp. 818–821.

Baker, et al., "Dexamethasone modulates binding and action of epidermal growth factor in serum–free . . . ", Proc. Natl. Acad Sci. USA, vol. 75, No. 4, Apr. 1978, pp. 1882–1886.

Bjare, "Serum–Free Cell Culture", Pharmac. Ther., vol. 53, 1992, pp. 355–375.

Clark, et al., "Optimizing Culture Conditions for the Production of A nimal Cells in Microcarrier Culture", Annals New York Academy of Sciences, pp. 33–46.

Cinatl Jr., et al., Protein–Free Culture of Vero Cells: A Substrate for Replication of Human Pathogenic Viruses, Cell Biology Intnl., vol. 17, No. 9, 1993, pp. 885–895.

Barnes, et al., "Serum–Free Cell Culture: a Unifying Approach", vol. 22, Dec. 1980, pp. 649–655.

Perusich, et al., "Virus Production in Microsphere–Induced Aggregate Culture of Animal Cells", Biotechnology Techniques, vol. 5, No. 2, 1991, pp. 145–148.

Hu, et al., "Selection of Microcarrier Diameter for the Cultivationo f Mammalian Cells on Microcarriers", vol. XXX, 1987, pp. 548–557.

Estes, et al., "Rotavirus Gene Structure and Function", Microbiological Reviews, Dec. 1989, pp. 410–449.

Suntharasamai, et al., "New Purified Vero–Cell Vaccine Prevents Rabies in Patients Bitten by Rabid Animals", The Lancet, Jul. 19, 1986, pp. 129–131.

Patton, et al., "Location of Intrachan Disulfide Bonds in the VP5* and VP8* Trypsin Cleavage Fragments . . . ", J. of Virology, vol. 67, No. 8, Aug. 1993, pp. 4848–4855.

Bishop, "Development of candidate rotavirus vaccines", Vaccine, vol. 11, Issue 2, 1993, pp. 247–254.

Brock, et al., "Replacement of transferrin in serum–free cultures of mitogen–stimulated mouse lymphocytes . . . ", Immunology Letters, vol. 15, 1987, pp. 23–25.

(List continued on next page.)

*Primary Examiner*—Lynette R. F. Smith
*Assistant Examiner*—Robert A. Zeman
(74) *Attorney, Agent, or Firm*—Michael D. Yablonsky; Jack L. Tribble

(57) ABSTRACT

Defined serum-free, low protein media (LPKM), that supports 1) Vero cell growth for up to 20 passages, 2) Vero cell growth on microcarriers and 3) rotavirus production is provided. Maximum cell densities attained are 60–100% of that in serum-containing medium; the doubling time is equal to that for cells in serum containing medium. Rotavirus titers achieved in LPKM-1 are 50–100% of the serum-containing process. Finally, since LPKM-1 contains no animal-sourced proteins, the problems associated with the serum-containing rotavirus production process (i.e. lengthy wash steps before infection, potential introduction of adventitious agents and lot-to-lot variability) can be avoided; while maintaining nearly equivalent product titers.

2 Claims, 3 Drawing Sheets

OTHER PUBLICATIONS

Christy, et al., "Evaluationof a Bovine–Human Rotavirus Reassortant Vaccine in Infants", J. Infect. Dis., vol. 168, 1993, pp. 1598–1599.

Clark, et al., "Immune P rotection of Infants against Rotavirus Gastroenteritis by a Serotype 1 Reassortant . . . ", J. of Infect. Dis., vol. 161, 1990, pp. 1099–1104.

Offit, et al., "Rotavirus–Specific Humoral and Cellular Immune Response after Primary, Symptomatic Infection", J. of Infect. Dis., vol. 167, 1993, pp. 1436–1440.

Konno, et al., "Proteolytic Enhancement of Human Rotavirus Infectivity", Clinical Infectious Diseases, vol. 16, Suppl. 2, 1993, pp. S92–S97.

Desselberger, "Towards Rotavirus Vaccines", Medical Virology, vol. 3, 1993, pp. 15–21.

Madeley, et al., "Viruses and diarrhoea—where are we now?", APMIS, vol. 101, 1993, pp. 497–504.

Estes, et al., "Rotavirus Stability and Inactiation", J. Gen. Virol., vol. 43, 1979, pp. 403–409.

Swanson, et al., "Characterization of Vero cells", J. of Biol. Standardization, vol. 16, 1988, pp. 311–320.

MacPherson, et al., "Agar Suspension Culture for the Selective Assay of Cells Transformed by Polyoma Virus", Virology, vol. 23, 1964, pp. 291–294.

Darfler, et al., "A Protein–Free Medium for the Growth of Hybridomas and Other Cells of the Immune System", In Vitro Cell. Dev. Biol., vol. 26, Aug. 1990, pp. 769–778.

Montagnon, "Polio and Rabies Vaccines Produced in Continuous Cell Lines: A Reality for Vero Cell Line", Develop Biol. Standard., vol. 70, 1989, pp. 27–47.

Litwin, "The growth of Vero cells in suspension as cell–aggregates in serum–free media", Cytotechnology, vol. 10, 1992, pp. 169–174.

Franek, et al., "Hydridoma growth and monoclonal antibody production in iron–rich protein–free medium . . . ", Cytotechnology, vol. 7, 1991, pp. 33–38.

Montagnon, et al., "The Large–Scale Cultivation of Vero Cells in Micro–Carrier Culture for Virus Vaccine Production . . . ", Develop. Biol. Standard., vol. 47, 1981, pp. 55–64.

Taub, et al., "The Development of Serum–Free Hormone Supplemented Media for the Primary Kidney . . . ", Ann. N.Y. Acad. Sci., 1981, pp. 406–421.

Clark, et al., "Serum Supplements and Serum–Free Media: Applicability for Microcarrier Culture . . . ", Developments in Biological Standardization, vol. 50, pp. 81–91.

* cited by examiner though use of serum in production processes is undesirable because of the potential for introducing adventitious agents and lot-to-lot variability in cell growth and virus production.

SERUM-FREE, LOW-PROTEIN MEDIA FOR ROTAVIRUS VACCINE PRODUCTION

CROSS-REFERENCE TO RELATED APPLICATIONS

This application claims the benefit of U.S. Provisional Application No. 60/063,301, filed Oct. 27, 1997, the contents of which are incorporated herein by reference in their entirety.

STATEMENT REGARDING FEDERALLY-SPONSORED R&D

Not applicable.

REFERENCE TO MICROFICHE APPENDIX

Not applicable.

FIELD OF THE INVENTION

Rotavirus Vaccines.

BACKGROUND OF THE INVENTION

Rotaviruses are the most common cause of acute infantile gastroenteritis. Rotavirus-induced disease is estimated to cause one million deaths of children under age two worldwide each year (Bishop 1993; Desselberger 1993). In the United States alone, approximately 200,000 hospitalizations and 150 deaths of children in this age cohort are attributable to rotavirus infection annually (for review, see Bishop 1993; Desselberger 1993). Rotavirus infections are so prevalent that nearly all children are seropositive by age three (Bishop 1993; Madeley 1993).

Natural rotavirus infection induces both humoral and cell mediated immune responses (Offit et al. 1993). Repeated infections with other serotypes produce only mild symptoms, if any (Bishop 1993). This evidence, together with the prevalence of infection and severe consequences of rotavirus diease has motivated rotavirus vaccine development. Several candidate vaccines, including those composed of live attenuated human, simian or bovine strains, reassortants of human and simian or bovine strains or recombinant subunits are in preclinical or clinical development.

One such vaccine, a bovine-human reassortant rotavirus adapted to replicate in Vero cells, induced protective immunity to severe disease in over 85% of vaccinees in recent clinical trials (Clark et al. 1990; Christy et al. 1993). Exemplary rotavirus reassortants and combinations thereof and their use in vaccines are found in U.S. Pat. No. 5,626, 851, May 6, 1997, and in U.S. Pat. No. 5,750,109, May 12, 1998, both of which are incorporated herein by reference in their entireties.

Vero cells, a continuous African Green Monkey Kidney cell line, (Swanson et al. 1988) have been known and used in the art for the production of human viral vaccines including poliovirus and rabies virus for many years (Montagnon et al. 1981; Suntharasami et al. 1986; Montagnon 1989). The cells are well-characterized and have an excellent safety record. These cells can be propagated in static culture and in suspension culture as cell aggregates (Litwin 1992; Perusich et al. 1991) or on microcarriers (Clark and Hirtenstein 1981); the latter processes being more readily scalable.

Rotaviruses require a tryptic cleavage of one of the two major outer coat proteins, VP4, to efficiently infect Vero cells in vitro (Estes et al., 1979; Estes and Cohen 1989; Konno et al., 1993; Patton et al., 1993). Previously, the production of reassortant rotaviruses required that Vero cells first be grown in serum-containing medium, then washed to remove serum proteins that otherwise reduce infectivity, and finally infected in serum-free basal medium containing trypsin. To simplify the virus production process and to avoid problems associated with serum-containing processes (e.g. the risk of introducing adventitious agents and the potential for lot-to-lot variability), we developed defined, serum-free, low protein media that are devoid of animal-sourced proteins. These media, called LPKM-1, LPKM-2 and LPKM-3, support the growth of Vero cells in static and microcarrier cultures and also support the production of rotaviruses to levels approaching that of serum-containing media.

SUMMARY OF THE INVENTION

Defined serum-free, low protein media provided herein, supports 1) Vero cell growth for up to 20 passages, 2) Vero cell growth on microcarriers and 3) rotavirus production. We refer to media as LPKM. Maximum cell densities attained are 60–100% of that in serum-containing medium and the mean doubling time is equal to serum containing medium. Rotavirus titers achieved in LPKM-1 are 80–100% of the serum-containing microcarrier process. Since LPKM media contain no animal-sourced proteins, the problems associated with the serum-containing rotavirus production process (i.e. lengthy wash steps before infection, potential introduction of adventitious agents and lot-to-lot variability of serum) are avoided while maintaining nearly equivalent product titers.

DETAILED DESCRIPTION OF THE INVENTION

Figure 1A:
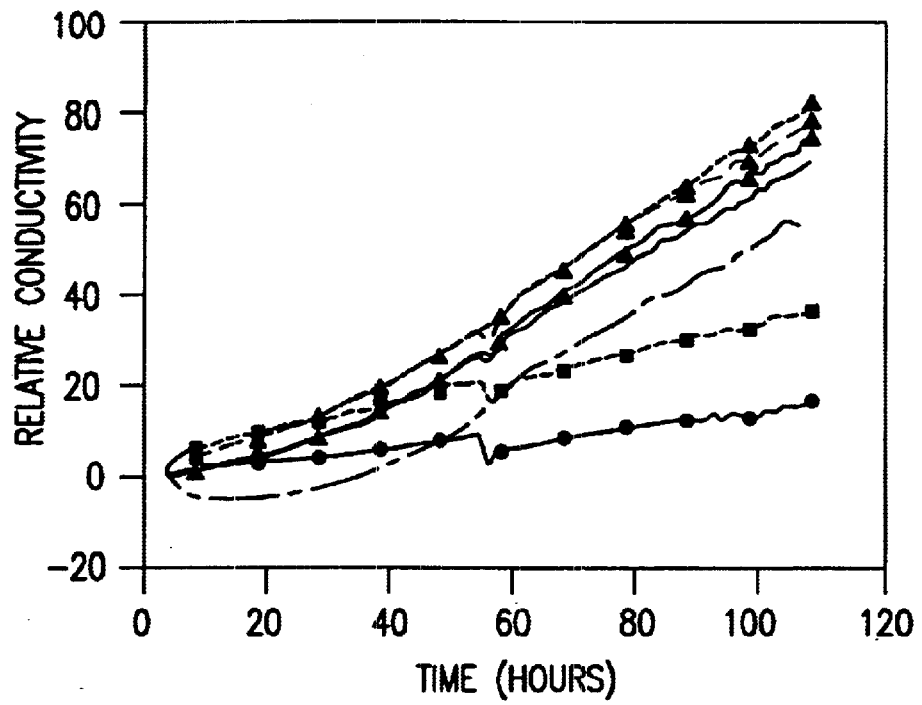
FIGS. 1A and 1B shows the Growth of Vero cells in K-1 medium with various concentrations of rhEGF and dex. Panel 1A shows relative conductivity, as measured by the Cellstat™ system, for cells grown in 10×rhEGF (---▲---),10× rhEGF and 4×dex (—▲—), 10×rhEGF and 1×dex (-▲-), 1×rhEGF and 4×dex (—), 1×rhEGF and 1×dex (-----), 4×dex only (---■---), and in K-1 without additives (—●—). Data shown are the average of triplicate wells. Panel 1B shows cell densities expressed as percent of FBS control, obtained 5 days after inoculation of Vero cells into K-1 medium containing various concentrations of rhEGF and dex. Shading of the bars corresponds to rhEGF concentration: ▨ no rhEGF, ▦ 1×rhEGF, ■ 10×rhEGF. Bars shown are the average of cell counts from duplicate wells.
Figure 1B:
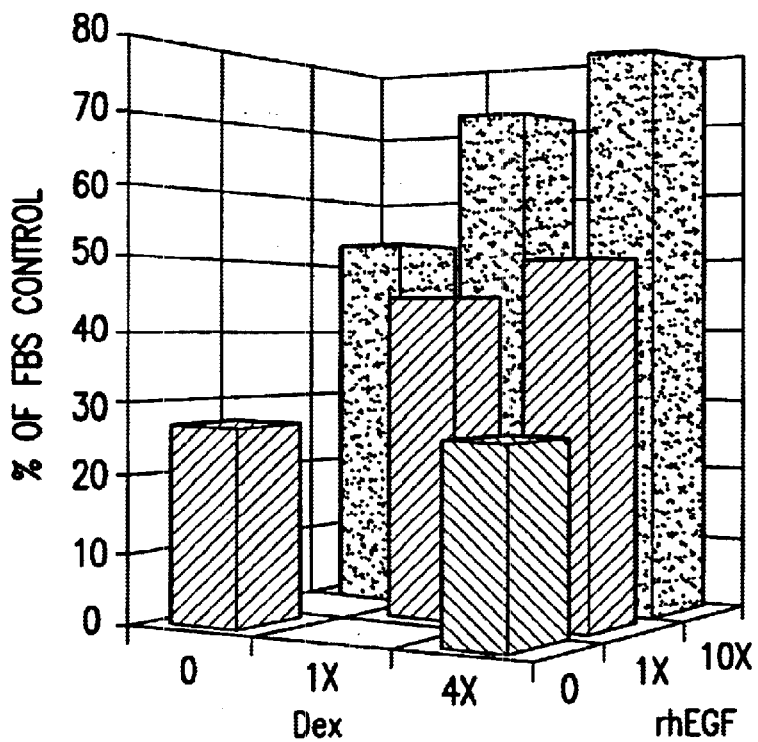
Figure 2:
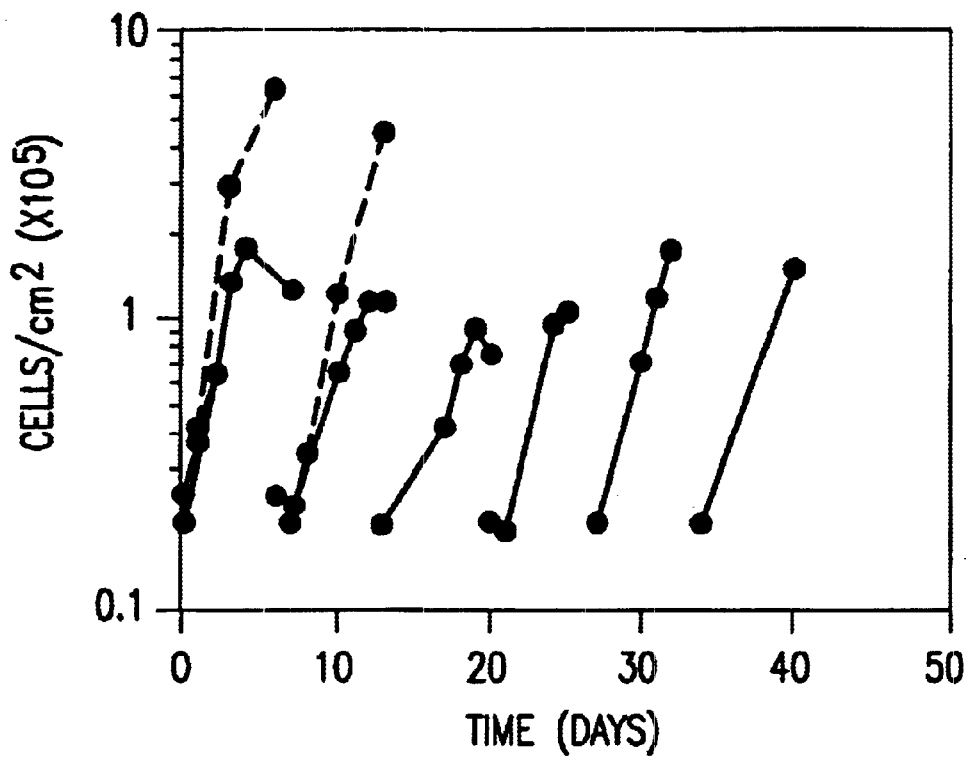
FIG. 2 shows the sequential passing of Vero cells in static culture 10% FBS-containing medium (---●---) and K-1 containing rhEGF and dex (—●—). For each passage, cells were plated at $2\times10^5$ cells/cm$^2$ and counted every 1–3 days. Cells from the previous passage were harvested at either the late-log or stationary phase of cell growth and used to begin the next passage.
Figure 3:
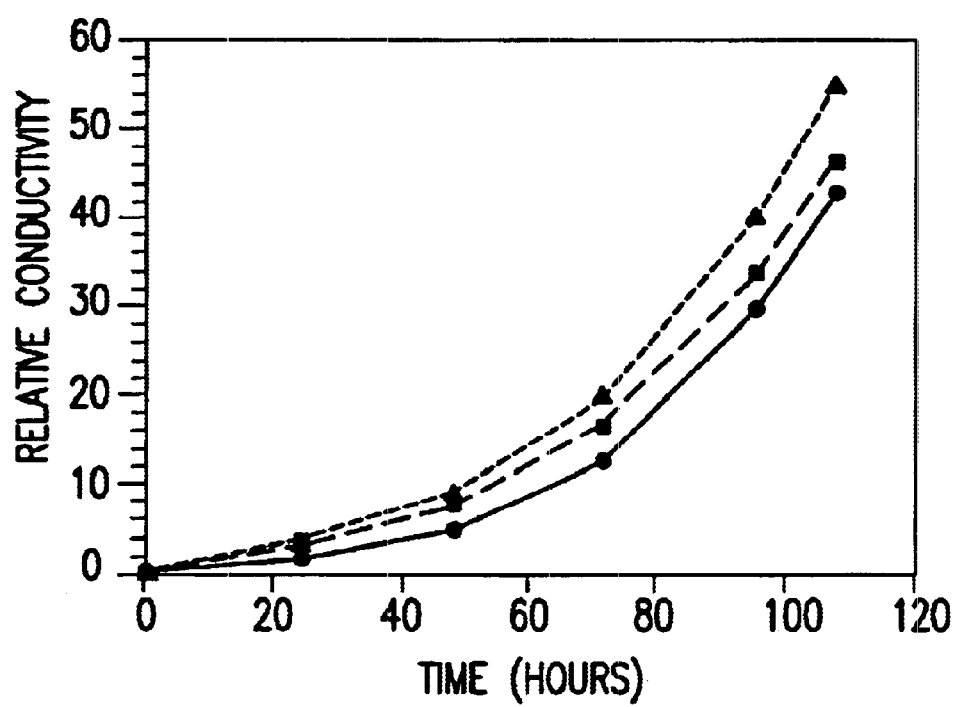
FIG. 3 shows the passage 4 growth of Vero cells in K-1+rhEGF/dex in the presence or absence of exogenous iron. Cells were plated at $2\times10^5$ cells/cm$^2$ in 24-well plates in media containing no exogenous iron (---▲---) or with added transferrin (—●—) or ferric citrate (--■--). Data shown are the average relative conductivity of triplicate wells measured by the Cellstat™ system.
Figure 4:
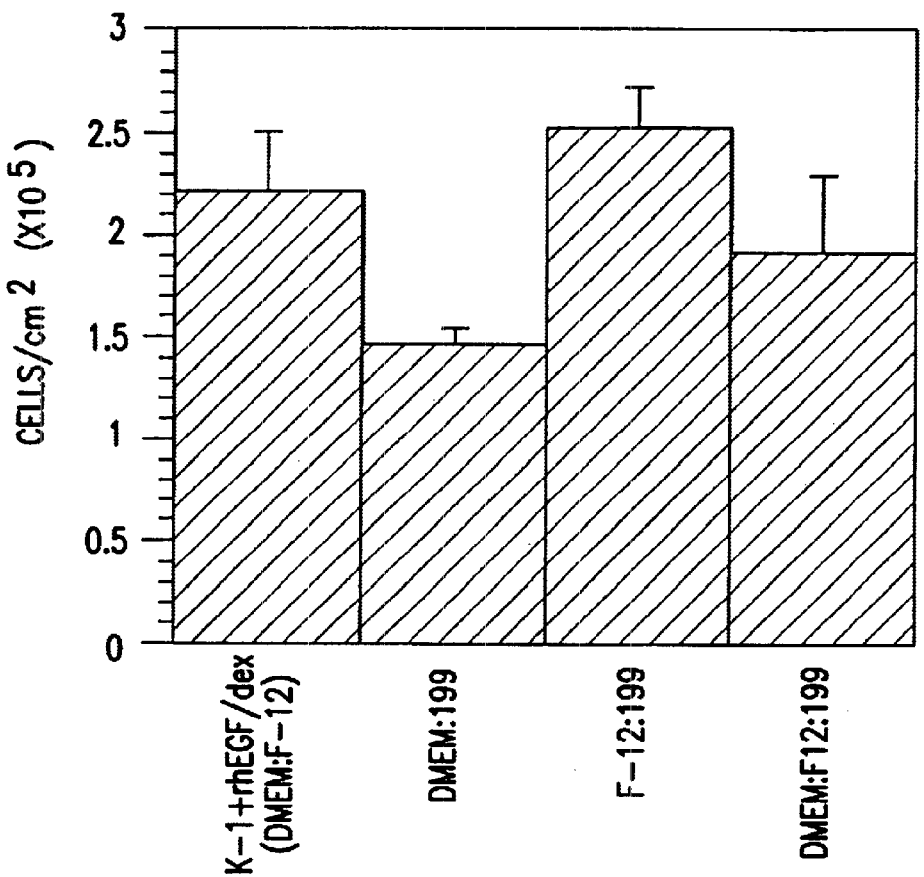
FIG. 4 shows the effect of basal media mixtures on Vero cell growth. Cells were plated at $2\times10^5$ cells/cm$^2$ in 24-well plates and counted 5 days post-plating. Media mixtures were supplemented as for K-1+rhEGF/dex. Results shown are means+/–S.D. of duplicate wells.
Figure 5:
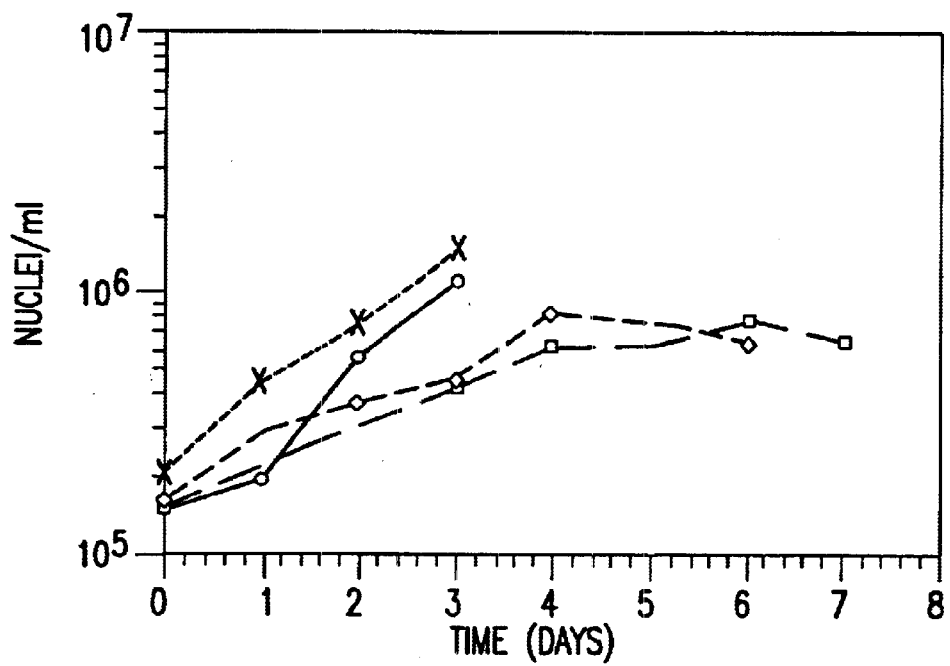
FIG. 5 shows the growth of Vero cells on Cytodex 1 microcarriers in four media, K-1+rhEGF/dex (-□-), LPKM-1 (--♦--), LPKM-2 (--✕--) and in 10% serum-containing medium (—⊖—). Cells were inoculated at 1.5–2.0×10$^5$ cells/ml and counted every 1–3 days using a nuclei staining technique.

Serum-free, low protein media are provided by the present invention. The media support Vero cell growth in static and agitated environments on standard cell culture surfaces and support rotavirus production. These media are referred to herein as LPKM-1, -2 and -3.

LPKM media contain many of the supplements found in K-1 medium (Taub and Livingston 1981). However, K-1 alone was not sufficient to sustain Vero cell growth for multiple passages. By adding recombinant human Epidermal Growth Fetor (rhEGF) and dexamethasone (dex), it is possible to directly transfer Vero cells to this medium (called K-1+rhEGF/dex) and sequentially subculture them at least 20 times (53 PDL). Dex and rhEGF have been shown to act synergistically to stimulate proliferation of primary human diploid fibroblasts (Baker et al. 1978) and have been used in serum-free media designed to support clonal growth and repeated passages of human diploid fibroblast cell lines (Bettger et al. 1981). Further improvements were made by changing the mixture of basal media from F-12: DMEM to F-12: Medium 199, which resulted in increased growth rates and final cell densities.

Animal sourced proteins were removed or replaced in LPKM-1. When possible, recombinant proteins expressed in *Escherichia coli* replaced animal-sourced proteins. Transferrin has long been recognized as a necessary component of serum-free medium for the growth of many different cell lines (Barnes and Sato 1980; Bjare 1992). However, some cells can use inorganic iron and chelated iron, e.g. ferric citrate (Franek and Dolnikova 1991), sodium nitroprusside (Darfler 1990) and pyridoxal isonicotinoyl hydrazone (Brock and Stevenson 1987). We have found that Vero cells grow in the absence of transferrin in 1:1 mixtures of DMEM:F-12 and F-12:199. No additional iron was required to replace transferrin. The combination of ferrous and ferric salts found in F-12: DMEM and F-12: Medium 199 presumably provide sufficient iron to support Vero cell growth.

Vero cells grown in static culture in LPKM-1 grew more slowly and attained a lower saturation density than did Vero cells grown in serum-containing medium. It is not known whether the increased doubling time is due to a general lengthening of the cell cycle, or if a smaller but constant proportion of cells proliferate in LPKM-1 at each passage. The modification of glucose, sodium bicarbonate, and sodium pyruvate concentrations in LPKM-2 resulted in Vero cell growth rate and maximum cell density in microcarrier culture equal to those reported in serum-containing medium. The addition of several trace elements, 2-mercaptoethanol, ethanolamine and the modification of some vitamin concentrations in LPKM-3 have yielded improvements in Vero cell growth in static culture.

Merten et al. (1994) have reported that a serum-free medium containing 40 mg/l protein (MDSS2) was able to support Vero cell growth in static and agitated environments. Vero cells were subcultured a total of 19 times and achieved the same growth rate as cells in their serum-containing control. However, the reported growth rate of cells in. MDSS2, 0.0098+/−0.0014 h$^{-1}$ (71 h doubling time), is 40% less than that for Vero-cells in LPKM-1 (0.017 h$^{-1}$). The maximum cell density attained in LPKM without a medium exchange is only about 85% of that in serum-containing medium. Clark et al. (1982) have suggested that Vero cells grown in serum-free media reach a lower saturation density because each cell spreads over a larger surface area. However, Vero cells grown in protein-free medium on polyvinyl formal (PVF)-treated surfaces reach saturation densities comparable to cells in serum-containing medium (Cinatl et al. 1993). These findings indicate that saturation density is a function of both the cell/substrate interaction and the medium composition.

We believe that this is the first report of rotavirus production using completely defined, serum-free, low protein (5 mg/l) media for both Vero cell growth and rotavirus production. The yield per cell of rotavirus in LPKM without a medium exchange was nearly equivalent to that for cells grown in serum-containing medium. The reduced virus titer was a reflection of the lower cell densities reached in the absence of a medium exchange. The virus stock was generated as follows: Vero cells were grown in serum-containing medium, washed extensively with phosphate buffered saline, then infected in serum-free basal medium containing trypsin. Although other viruses have been adapted to growth in serum-free media by repeated passaging, the possibility of adapting the rotavirus to propagate better in LPKM-1 was not explored.

Recently, other viruses have been produced using Vero cells grown in serum-free media. Maximal rabies virus titers in MDSS2 were 1.5-fold greater and were acheived 1–2 days earlier than in serum-containing medium (Merten et al. 1994). The titers of Coxsackievirus, poliovirus (3 strains), measles virus and Herpes simplex virus (2 strains) produced from Vero cells grown in PFEK-1, a protein-free medium, were also shown to be similar to titers produced in a serum-containing process (Cinatl et al. 1993). However, viral titers obtained from cells grown in PFEK-1 were equal to those from cells grown in serum-containing medium only when cells were grown on PVF-treated surfaces.

Because vaccines are generally administered to healthy individuals, the safety of the product is a primary concern. By eliminating animal-sourced proteins from LPKM media, the risk of introducing adventitious agents is reduced. We have also demonstrated that a tumorigenic phenotype is not induced in Vero cells, as measured by colony formation in soft agar, when sequentially passaged in serum-free medium. Finally, LPKM media contains only defined chemical components and recombinant proteins, thereby providing for improved lot-to-lot and process consistency.

EXAMPLE 1

Media and Chemicals

Media (Dulbecco's Modified Eagle's Medium, Medium 199 and Nutrient Mixture F-12), dexamethasone (dex), hydrocortisone (HC), and triiodothyronine (T3) were from Sigma Chemical Company (St. Louis, Mo.). Recombinant human epidermal growth factor (rhEGF) was from R&D Systems (Minneapolis, Minn.), and prostaglandin $E_1(PGE_1)$ was from BioMol (Plymouth Meeting, Pa.). Fetal bovine serum (FBS) and GlutaMax I were from Gibco (Grand Island, N.Y.). L-glutamine was from Mediatech (Washington, D.C.) or JRH (Lenexa, Kans.).

Media Formulation

The compositions of LPKM media are provided in Table 1. Media of this invention can be formulated by standard methods known in the art. For convenience, a formulation for LPKM-1 is provided in Table 2. LPKM-2 and LPKM-3 can be similarly formulated by modifying the concentrated solutions shown for formulating LPKM-1. Alternatively, additional components can be added separately or individually, as will be understood by one of skill in the art.

EXAMPLE 2

Cell Propagation in Static Culture

Vero cells (ATCC, CCL-#81, passage 121) were grown either in Dulbecco's Modified Eagle's Medium (DMEM) with 10% FBS and 2 mM L-glutamine or in serum-free media with 2 mM L-glutamine. Cells were used between passages 123 and 146. K-1 serum-free medium was prepared as previously described (Taub and Livingstson, 1981). Other additives to the serum-free media were prepared as follows: rhEGF was reconstituted according to manufacturer's protocol, except that albumin was omitted from the reconsititution medium; dex was dissolved at 1 mg/ml in absolute ethanol. Final media concentrations of all components are as stated in the LPKM recipe table (Table 1). rhEGF and all hormones were stored at −20° C. and were frozen and thawed a maximum of two times.

For cell growth and virus production in static culture, Vero cells were grown in 75 cm$^2$ cell culture flasks (Corning/Costar, Cambridge, Mass.). Cells were subcultured using 0.25% trypsin/1 mM EDTA solution, and plated at 1.3–4.0× 10$^4$ cells/cm$^2$. For cells in serum-containing medium, trypsin/EDTA was removed prior to cell detachment and cells were resuspended in an appropriate volume of serum-containing medium after detachment. For cells in serum-free medium, the trypsin/EDTA was not removed prior to cell detachment. Trypsin activity was quenched with an equal volume of a 1 mg/ml soybean trypsin inhibitor (STI) (Gibco) solution. The resulting cell suspension was centrifuged at 250× g for 10 minutes, the supernatant aspirated, and the cell pellet resuspended in an appropriate volume of serum-free medium. Cell viability was determined by exclusion of trypan blue dye (0.4%, diluted 1:1 with the cell suspension) and cell numbers were determined using a hemacytometer. Verification of improved cell density and/or growth rate was obtained by growing the cells for at least three passages in the media or additives identified in the screens.

EXAMPLE 3

Growth on Microcarriers

Microcarrier experiments were conducted in siliconized 250 ml spinner flasks (Bellco Microcarrier Flask) using Cytodex I microcarriers (Pharmacia) at a concentration of 3 g/l. Microcarriers were rehydrated and sterilized according to the manjufacturer's recommendations. After sterilization, beads were rinsed once with growth medium prior to inoculation. Cultures were inoculated with 1–2×10$^5$ cells/ml using cells grown in 225 cm$^2$ cell culture flasks (Corning/Costar). After inoculation, the cultures were agitated at 35 rpm throughout both the cell growth and virus infection phases. Cultures were sampled daily for cell counts. Briefly, microcarriers were allowed to settle and the medium gently removed. An equal volume of crystal violet solution (Hu and Wang 1987) was added and the solution incubated at 37° C. for 30 minutes. The solution was then vigorously vortexed and the nuclei counted using a hemacytometer.

EXAMPLE 4

Screening of Media and Additives

The effect of media or additives on final cell density was determined using the following method. Cells were plated in duplicate wells for each test condition at a density of 2×10$^4$ cells/cm$^2$ in 24-well plates. After incubation at 37° C. for 5 days, cells were removed using 0.5 ml trypsin/EDTA per well. Trypsin activity was quenched by adding 0.5 ml of 1 mg/ml STI and the cells thoroughly resuspended. Cell viability and concentration were determined as described above.

In some cases, cell growth was monitored using a Cellstat™ system (Cellstat Technologies, Palo Alto, Calif.). Cells were plated in triplicate wells for each test condition in 24-well plates at 2×10$^4$ cells/cm$^2$. A Bioprobe™ lid was sterilized according to manufacturer's directions and placed on the 24-well plate. The lid and plate were then inserted into a measurement board located in an incubator. Cells were incubated for 5–7 days in a humidified atmosphere of 5% $CO_2$. Medium conductivity in each well was automatically measured and recorded every hour and a growth curve generated. The slopes of the growth curves were used as an indicator of relative growth rate.

EXAMPLE 5

Tumorigenicity

Tumorigenicity testing was done using colony growth in soft agar using standard techniques known in the art. (MacPherson and Montaigrier 1964).

EXAMPLE 6

Virus Infection

A bovine-human reassortant rotavirus known in the art was used in experiments (F. Clark, Children's Hospital of Philadelphia) (U.S. Pat. No. 5,626,851, May 6, 1997). Bovine rotavirus strain WC3 and human rotavirus strain W179, which contains the G serotype 1 outer capsid protein, were used to coinfect MA104 (fetal green monkey kidney) cells. Progeny virus were plaque purified and a strain, W179-9, identified in which only the VP7 (or G) gene segment is derived from the human rotavirus strain. Vero cells used for infection were maintained between passages 125 and 138. Cells growing in serum-containing medium in cell culture flasks were rinsed twice with Dulbecco's Phosphate Buffered Saline (D-PBS) (approximately 2 minutes per wash) before infection. DMEM containing 2 mM L-glutamine but no FBS was added prior to infection. For serum-containing microcarrier cultures, cells were washed three times with D-PBS. Each wash consisted of a 30–45 minute incubation with agitation at 37° C. After washing, one volume of DMEM with 2 mM L-glutamine was added and the cells were infected. Cells propagated in serum-free media were sometimes washed with D-PBS and the medium changed to DMEM with 2 mM L-glutamine. In other cases, either 75% of the medium was removed and replaced with an equal volume of fresh medium immediately prior to infection or the medium was not exchanged. Virus was added from a stock solution at a multiplicity of infection (MOI) of 0.5. Trypsin/NaCl (Gibco), at 12.5 or 25 mg/ml, was added immediately after the virus inoculum. Infected cultures were either incubated at 37° C. or switched to 34° C. immediately after infection.

Cultures were sampled daily for 3–5 days following infection. One ml samples were removed and stored at −70° C. until assay.

EXAMPLE 7

Rotavirus Plague Assay

Rotavirus titers were determined using an agarose overlay plaque assay procedure and MA-104 cells (fetal green monkey kidney, MA Bioproducts) as is known in the art. Briefly, samples were diluted from $10^{-1}$ to $10^{-7}$ in DMEM with 2 mM L-glutamine. 100 µl of dilutions from $10^{-5}$ to $10^{-7}$ were applied in duplicate wells to confluent monolayers of MA-104 cells in 6-well plates and incubated for 1 hour in a humidified atmosphere of 5% $CO_2$. After incubation, a 1:1 mixture of 1% agarose and 2×MSO (690 ml distilled, deionized water, 200 ml 10×Earle's Balanced Salt Solution, 20 ml 100×BME amino acid solution, 20 ml 100×MEM vitamins, 20 ml 200mM L-glutamine, 50 ml 5% sodium bicarbonate solution, all from Gibco) with 1.58 USP units of trypsin/ml was layered over the cells, and the plates were incubated undisturbed for 3 days at 37° C. in a humidified atmosphere of 5% $CO_2$. To visualize the plaques, a 1:1 mixture of 2×Earle's Balanced Salt Solution and 1% agarose containing 0.1 g/l neutral red was layered over the agarose/MSO layer and incubated for another 24 hours. Plaques were visualized as unstained areas in the red-stained monolayer.

TABLE 1

Composition of LPKM-1, -2 and-3

| Formulation-> Component | LPKM-1 mg/l | LPKM-2 mg/l | LPKM-3 mg/l |
|---|---|---|---|
| INORGANIC SALTS | | | |
| Ammonium Metavanadate | 0 | 0 | 0.00117 |
| Calcium Chloride/CaCl2 (anhyd.) | 116.6 | 116.6 | 116.6 |
| Cupric Sulfate/CuSO4.5H2O | 0.00125 | 0.00125 | 0.00125 |
| Ferric Nitrate/Fe(NO3)3.9H2O | 0.36 | 0.36 | 0.36 |
| Ferrous Sulfate/FeSO4.7H2O | 0.415 | 0.415 | 0.415 |
| Magnesium Chloride/MgCl2 (anhyd.) | 28.61 | 28.61 | 28.61 |
| Magnesium Sulfate/MgSO4 (anhyd.) | 49 | 49 | 49 |
| Manganese Sulfate | 0 | 0 | 0.000151 |
| Molybdic Acid.4H2O (ammonium) | 0 | 0 | 0.00124 |
| Potassium Chloride/KCl | 311.8 | 311.8 | 311.8 |
| Sodium Acetate/CH3CO2Na (anhydrous) | 25 | 25 | 25 |
| Sodium Bicarbonate/NaHCO3 | 1688 | 3688 | 3688 |
| Sodium Chloride/NaCl | 7199.5 | 7199.5 | 7199.5 |
| Sodium Phosphate Dibasic/Na2HPO4 (anhyd.) | 71 | 71 | 71 |
| Sodium Phosphate Monobasic/NaH2PO4 (anhyd.) | 70 | 70 | 70 |
| Zinc Sulfate/ZnSO4.7H2O | 0.43 | 0.43 | 0.43 |
| AMINO ACIDS | | | |
| L-Alanine | 16.95 | 16.95 | 16.95 |
| L-Arginine.HCl | 140.5 | 140.5 | 140.5 |
| L-Asparagine.H2O | 7.5 | 7.5 | 7.5 |
| L-Aspartic acid | 21.5 | 21.5 | 21.5 |
| L-Cysteine.HClH2O | 17.55 | 17.55 | 17.55 |
| L-Cystine.2HCl | 13 | 13 | 13 |
| L-Glutamic acid | 44.85 | 44.85 | 44.85 |
| L-Glutamine | 1.0 mM | 1.0 mM | 1.0 mM |
| Glycine | 28.75 | 28.75 | 28.75 |
| L-Histidine.3HCl.H2O | 21.5 | 21.5 | 21.5 |
| L-Hydroxyproline | 5 | 5 | 5 |
| L-Isoleucine | 22 | 22 | 22 |
| L-Leucine | 36.5 | 36.5 | 36.5 |
| L-Lysine.HCl | 53.25 | 53.25 | 53.25 |
| L-Methionine | 9.75 | 9.75 | 9.75 |
| L-Phenylalanine | 15 | 15 | 15 |
| L-Proline | 37.25 | 37.25 | 37.25 |
| L-Serine | 17.75 | 17.75 | 17.75 |
| L-Threonine | 21 | 21 | 21 |
| L-Tryptophan | 6 | 6 | 6 |
| L-Tyrosine.2Na.2H2O | 32.9 | 32.9 | 32.9 |
| L-Valine | 18.35 | 18.35 | 18.35 |
| VITAMINS | | | |
| Ascorbic acid.Na | 0.025 | 0.025 | 0.0533 |
| D-Biotin | 0.0085 | 0.0085 | 0.0085 |
| Calciferol/Vitamin D-2 | 0.05 | 0.05 | 0.05 |
| Choline Chloride | 7.25 | 7.25 | 7.25 |
| Folic Acid | 0.655 | 0.655 | 0.655 |
| myo-Inositol | 9.025 | 9.025 | 18.025 |
| Menadione | 0.005 | 0.005 | 0.021 |
| Niacinamide | 0.0325 | 0.0325 | 0.0325 |
| Nicotinic Acid/Niacin | 0.0125 | 0.0125 | 0.0125 |
| p-Amino Benzoic Acid | 0.025 | 0.025 | 0.025 |
| D-Pantothenic Acid (hemi-calcium) | 0.255 | 0.255 | 0.255 |
| Pyridoxal.HCl | 0.0125 | 0.0125 | 0.0375 |
| Pyridoxine.HCl | 0.0425 | 0.0425 | 0.0425 |
| Retinol/Vitamin A (acetate) | 0.07 | 0.07 | 0.07 |
| Riboflavin | 0.025 | 0.025 | 0.025 |
| D,L-Alpha Tocopherol phosphate.Na | 0.005 | 0.005 | 0.005 |
| Thiamine.HCl | 0.155 | 0.155 | 0.155 |
| Vitamin B-12 | 0.7 | 0.7 | 0.7 |
| OTHER | | | |
| Adenine sulfate | 5 | 5 | 5 |
| Adenosine-5-triphosphate.2Na | 0.5 | 0.5 | 0.5 |
| Adenosine-5-monophosphate.Na | 0.1 | 0.1 | 0.1 |
| Cholesterol | 0.1 | 0.1 | 0.1 |
| 2-deoxy-D-Ribose | 0.25 | 0.25 | 0.25 |
| D-Ribose | 0.25 | 0.25 | 0.25 |
| D-Glucose (Dextrose) | 1400 | 3000 | 3000 |
| Glutathione (reduced) | 0.025 | 0.025 | 0.025 |
| Guanine.HCl | 0.15 | 0.15 | 0.15 |
| Hypoxanthine.Na | 2.585 | 2.585 | 2.585 |
| Linoleic Acid | 0.04 | 0.04 | 0.04 |
| D,L-Lipoic Acid | 0.105 | 0.105 | 0.105 |
| Phenol Red.Na | 10.6 | 10.6 | 10.6 |
| Putrescine.2HCl | 1.6905 | 1.6905 | 1.6905 |
| Pyruvic Acid.Na | 55 | 165 | 165 |
| Thymidine | 1.55 | 1.55 | 1.55 |
| Thymine | 0.15 | 0.15 | 0.15 |
| Tween 80/Polyoxyethylene-sorbitan Monooleate | 10 | 10 | 10 |
| Uracil | 0.15 | 0.15 | 0.15 |
| Xanthine.Na | 0.175 | 0.175 | 0.175 |
| ADDITIVES-Small Molecules | | | |
| Ethanolamine | 0 | 0 | 50 µM |
| Galactose | 2000 | 0 | 0 |
| Glutamax I (ala-gln) | 0.8 mM | 0.8 mM | 4.0 mM |
| 2-Mercaptoethanol | 0 | 0 | 55 µM |
| Nucleosides | | | |
| Adenosine | 3.5 | 3.5 | 3.5 |
| Uridine | 3.5 | 3.5 | 3.5 |
| Cytidine | 3.5 | 3.5 | 3.5 |
| Guanosine | 3.5 | 3.5 | 3.5 |
| Pluronic F-68 (to 0.1% w/v) | 1000 | 1000 | 1000 |
| ADDITIVES-Growth Factors/Hormones | | | |
| Dexamethasone | 0.2 | 0.2 | 0.2 |
| Epidermal Growth Factor (recombinant human) | 0.0033 | 0.0033 | 0.0033 |
| Hydrocortisone | 0.016 | 0.016 | 0.016 |
| Insulin (recombinant human, Zn Full Chain) | 5 | 5 | 5 |
| Prostaglandin E1 | 0.025 | 0.025 | 0.025 |
| Thiodothyronine (T3) | 0.000033 | 0.000033 | 0.000033 |

TABLE 2

LPKM-1 Formulation
Basal Medium:
1:1 Nutrient Mixture F-12 (Ham): Medium 199 with 4mM alanyl-glutamine
Gibco (Grand Island, NY)

| COMPONENT | mfr (location) | final medium concentration |
|---|---|---|
| Nucleosides: | | |
| thymidine | Sigma (St. Louis, MO) | 12 mg/l |
| adenosine | Sigma (St. Louis, MO) | 35 mg/l |
| uridine | Sigma (St. Louis, MO) | 35 mg/l |
| cytidine | Sigma (St. Louis, MO) | 35 mg/l |
| guanosine | Sigma (St. Louis, MO) | 35 mg/l |
| Putrescine | Sigma (St. Louis, MO) | 16.1 mg/l |
| Galactose | Sigma (St. Louis, MO) | 1 g/l |
| Hum recomb insulin | Gibco (Grand Island, NY) | 5 mg/l |

The following are supplied as sterile (gamma irradiated) powders. Reconstitute with sterile solutions as stocks.

| | | stock concentration/fold concentrate |
|---|---|---|
| rhEGF | R&D Systems (Minneapolis, MN) | 33 mg/ml/10,000X |
| dexamethasone | Sigma (St. Louis, MO) | 1 mg/ml/5,000X |
| PGE1 | BioMol (Plymouth Meeting, PA) | 250 mg/ml/10,000X |
| HC | Sigma (St. Louis, MO) | 160 mg/ml/10,000X |
| T3 | Sigma (St. Louis, MO) | 0.033 mg/ml/1,000,000X |

100X Supplement:

Dissolve nucleosides, putrescine, and galactose in water.
Filter sterilize and store at 4 C.
1,000X Supplement:
Combine and filter:

| 1.0 ml rhEGF | 10,000X stock solution |
|---|---|
| 1.0 ml Hydrocortisone | 10,000X stock solution |
| 1.0 ml PGE1 | 10,000X stock solution |
| 2.0 ml dexamethasone | 5,000X stock solution |
| 10 ul T3 | 1,000,000X stock solution |

Dilute to 10 ml in Nutrient Mixture F-12.
Filter and store at 4 C.
LPKM-1 Combine all the following aseptically:
1.0 l 1:1 F-12:Medium 199 (already contains 4 mM Ala-Gln)
5 ml 200 mM l-glutamine solution
12 10 ml 100X Supplement
1.0 ml 1000X hr Insulin solution
1.0 ml 1000X Supplement
10 ml 10.0% Pluronic F-68 Solution (for suspension cultures only)

TABLE 3

A Comparison of K-1 + rhEGF/dex and LPKM-1 Serum-free Media

| | K1 + rhEGF/dex | LPKM-1 | LPKM-2 | LPKM-3 |
|---|---|---|---|---|
| Basal media | DMEM: F12 | F12: Medium 199 | F12: Medium 199 | F12: Medium 199 |
| Protein[1] concentration source | 10 mg/l bovine | 5 mg/l recombinant | 5 mg/l recombinant | 5 mg/l recombinant |
| Microcarrier growth (% of FBS control)[2] | 35–50 50 | 60–85 100 | 100 100 | not determined |
| Max. density Growth rate | | | | |

TABLE 3-continued

A Comparison of K-1 + rhEGF/dex and LPKM-1 Serum-free Media

| | K1 + rhEGF/dex | LPKM-1 | LPKM-2 | LPKM-3 |
|---|---|---|---|---|
| Virus Production (% of FBS control)[3] using Microcarrier Process Cell-Specific Yield | 50 | 60–100 | 75–100 | not determined |
| Titer | 15–40 | 50–85 | 75–100 | |

[1]Protein composition of the media compared by both concentration and origin.
[2]Data presented are relative to Vero cell growth in serum-containing medium.
[3]Data presented are relative to virus production using a serum-containing process (see Materials and Methods). Upper limit of ranges presented were from cultures receiving a 75% medium exchange immediately prior to inoculation with virus.

Baker, J. B., Batsh, G. S., Carney, D. H. and Cunningham, D. D. Dexamethasone modulated binding and action of epidermal growth factor in serum-free cell culture. P.N.A.S. 75 (4): 1882–1886; 1978

Barnes, D. and Sato, G. Serum-free cell culture: A unifying approach. Cell. 22 649–655; 1980

Bettger, W. J., Boyce, S. T., Wathall, B. J. and Ham, R. G. Rapid clonal growth and serial passage of human diploid fibroblasts in a lipid-enriched synthetic medium supplemented with epidermal growth factor, insulin and dexamethasone. P.N.A.S. 78 (9): 5588–5592; 1981

Bishop, R. F. Development of candidate rotavirus vaccines. Vaccine. 11 (2): 247–254; 1993

Bjare, U. Serum-free cell culture. Pharmac. Ther. 53 355–374; 1992

Brock, J. H. and Stevenson, J. Repacement of transferrin in serum-free cultures of mitogen-stimulated mouse lymphocytes by a lipophilic iron chelator. Immunol. Lett. 15: 23–25; 1987

Christy, C., Offit, P., Clark, H. F. and Treanor, J. Evaluation of a bovine-human rotavirus reassortant vaccine in infants. J. Inf. Dis. 168 1598–1599; 1993

Cinatl, J., Cinatl, J., Rabenau, H., Rapp, J., Kornhuber, B. and Doerr, H. -W. Protein-free culture of Vero cells: A substrate for replication of pathogenic viruses. Cell Biology International. 17 (9): 885–895; 1993

Clark, H. F., Borian, F. E. and S. A. Plotkin. Immune protection against rotavirus gastroenteritis by a serotype 1 reassortant of bovine rotavirus WC3. J. Inf. Dis. 161: 1099–1104; 1990

Clark, J. M., Gebb, C. and Hirtenstein, M. D. Serum supplements and serum-free media: Applicability for microcarrier culture of animal cells. Develop. Biol. Standard. 30: 81–91; 1982

Clark, J. M. and Hirtenstein, M. D. Optimizing conditions for the production of animal cells in microcarrier culture. Ann. N.Y. Acad. Sci.33–46; 1981

Darfler, F. J. A protein-free medium for the growth of hybridomas and other cells of the immune system. In Vitro Cell. Devel. Biol. 26: 769–778; 1990

Desselberger, U. Towards rotavirus vaccines. Rev. Med. Virol. 3 (1): 15–21; 1993

Estes, M. K. and Cohen, J. Rotavirus gene structure and function. Microbiol. Rev. 53 (4): 410–449; 1989

Estes, M. K., Graham, D. Y., Smith, E. M. and Gerba, C. P. Rotavirus stability and inactivation. J. Gen. Virol. 43: 403–409; 1979

Franek, F. and Dolnikova, J. Hybridoma growth and monoclonal antibody production in iron-rich protein-free medium: Effect of nutrient concentration. -Cytotechnology. 7: 33–38; 1991

Hu, W. -S. and Wang, D. I. C. Biotechnology and Bioengineering. 30: 548–555; 1987

Konno, T., Suzuki, H., Kitaoka, S., Sato, T., Fukuhara, N., Yoshie, O., Fukudome, K. and Numazaki, Y. Proteolytic enhancement of human rotavirus infectivity. Clin. Inf. Dis. 16 (Suppl. 2): S92–97; 1993

Litwin, J. The growth of Vero cells in suspension as cell-aggregates in serum-free media. Cytotechnology. 10: 169–174; 1992

MacPherson, I. and Montaigner, L. Agar suspension culture for the selective assay of cells transformed by polyoma virus. Virology. 23: 291–294; 1964

Madeley, D. Viruses and diarrhoea- where are we now? APMIS. 101: 497–504; 1993

Merten, O. -W., Kierulff, J. V., Castignolles, N. and Perrin, P. Evaluation of the new serum-free medium (MDSS2) for the production of different biologicals: Use of various cell lines. Cytotechnology. 14: 47–59; 1994

Montagnon, B. J. Polio and rabies vaccines prduced in continuous cell lines: A reality for Vero cell line. Develop. Biol. Standard. 70: 27–47; 1989

Montagnon, B. J., Fanget, B. and Nicolas, A. J. The large-scale cultivation of Vero cells in micro-carrier culture for virus vaccine production: Preliminary results for killed poliovirus vaccine. Develop. Biol. Standard. 47 55–64; 1981

Offit, P., Hoffenberg, E. J., Santos, N. and Gouvea, V. Rotavirus-specific humoral and cellular immune response after primary, symptomatic infection. J. Inf. Dis. 167: 1436–1440; 1993

Patton, J. T., Hua, J. and Mansell, E. A. Location of intrachain disulfide bonds in the VP5* and VP8* trypsin cleavage fragments of the rhesus rotavirus spike protein VP4. J. Virol. 67 (8): 4848–4855; 1993

Perusich, C. M., Goetghebeur, S. and Hu, W. -S. Virus production in microshpere-induced aggregate culture of animal cells. Biotechnol. Tech. 5 (2): 145–148; 1991

Suntharasami, P., Warrell, M. J., Warrell, D. A., Viravan, C., Looareesuwan, S., W.Supanaranond, Chanthavanich, P., Supapochana, A., Tepsumethanon, W. and Pouradier-Dutiel, X. New purified Vero-cell vaccine prevents rabies in patients bitten by rabid animals. Lancet. (July 19): 129–131; 1986

Swanson, S. K., Mento, S. J., Weeks-Levy, C., Brock, B. D., Kowal, K. J., Wallace, R. E., Ritchey, M. B. and Cano, F. R. Characterization of Vero cells. J. Biol. Standard. 16: 311–320; 1988

Taub, M. and Livingston, D. The development of serum-free hormone-supplemented media for primary kidney cultures and their use in examining renal functions. Ann. N.Y. Acad. Sci. 406–421; 1981

What is claimed:

1. A Serum-free media for the production of rotavirus selected from the group consisting of LPKM-1, LPKM-2 and LPKM-3.

2. A method of producing a vaccine against rotavirus comprising, a) growing Vero cells in a media of claim 1;
b) infecting the cells with at least one strain of rotavirus, and
c) harvesting the rotavirus.

* * * * *